(12) United States Patent
Wu et al.

(10) Patent No.: US 11,586,958 B2
(45) Date of Patent: Feb. 21, 2023

(54) APPARATUSES, SYSTEMS, AND METHODS FOR MACHINE LEARNING USING ON-MEMORY PATTERN MATCHING

(71) Applicant: MICRON TECHNOLOGY, INC., Boise, ID (US)

(72) Inventors: Di Wu, Boise, ID (US); Anthony D. Veches, Boise, ID (US); James S. Rehmeyer, Boise, ID (US); Debra M. Bell, Boise, ID (US); Libo Wang, Boise, ID (US)

(73) Assignee: MICRON TECHNOLOGY, INC., Boise, ID (US)

( * ) Notice: Subject to any disclaimer, the term of this patent is extended or adjusted under 35 U.S.C. 154(b) by 424 days.

(21) Appl. No.: 16/840,916

(22) Filed: Apr. 6, 2020

(65) Prior Publication Data

US 2021/0312310 A1    Oct. 7, 2021

(51) Int. Cl.
*G06N 5/04*    (2006.01)
*G06N 5/047*    (2023.01)
*G06K 9/62*    (2022.01)
*G06N 20/00*    (2019.01)

(52) U.S. Cl.
CPC ........... *G06N 5/047* (2013.01); *G06K 9/6201* (2013.01); *G06N 20/00* (2019.01)

(58) Field of Classification Search
CPC ...... G06K 9/6201; G06K 9/62; G06K 9/6217; G06K 9/6256; G16H 50/70; G16H 50/20; G06N 20/10; G06N 3/08; G06N 5/047; G06N 3/0454; G06N 20/00; G06N 5/003; G06N 5/04; G06V 10/94; G06V 10/75; G06V 10/70; G06V 10/766; G06V 10/774; G06V 30/191; G06V 30/19147

USPC ................... 706/12, 20, 26, 27, 45; 382/159
See application file for complete search history.

(56) References Cited

U.S. PATENT DOCUMENTS

| | | | | |
|---|---|---|---|---|
| 9,525,696 | B2* | 12/2016 | Kapoor | G06F 16/2358 |
| 9,800,608 | B2* | 10/2017 | Korsunsky | G06F 21/55 |
| 10,002,668 | B2* | 6/2018 | Son | G11C 16/102 |
| 10,580,481 | B1 | 3/2020 | Sadredini et al. | |
| 10,613,795 | B2* | 4/2020 | Oh | G11C 16/26 |
| 10,789,280 | B2* | 9/2020 | Roy | G06F 9/54 |
| 10,803,919 | B2* | 10/2020 | Kim | G11C 11/406 |
| 10,929,748 | B1* | 2/2021 | Morten | G06N 3/0635 |
| 11,068,641 | B1* | 7/2021 | Wu | G06F 30/398 |
| 11,152,067 | B2* | 10/2021 | Choi | G11C 19/08 |
| 11,296,717 | B2* | 4/2022 | Fick | H03F 3/45968 |
| 11,327,826 | B1* | 5/2022 | Shama | H04L 41/147 |
| 11,360,932 | B2* | 6/2022 | Fick | H04L 45/38 |
| 11,393,531 | B2* | 7/2022 | Manning | G11C 11/4091 |
| 11,442,940 | B2* | 9/2022 | Bell | G11C 11/407 |
| 2015/0279466 | A1 | 10/2015 | Manning | |

(Continued)

OTHER PUBLICATIONS

ISR/WO dated Jul. 9, 2021 for PCT Appl. No. PCT/US2021/023250.

*Primary Examiner* — Andrew Joseph Rudy
(74) *Attorney, Agent, or Firm* — Dorsey & Whitney LLP

(57) ABSTRACT

Embodiments of the disclosure are drawn to apparatuses, systems, methods for performing operations associated with machine learning. Machine learning operations may include processing a data set, training a machine learning algorithm, and applying a trained algorithm to a data set. Some of the machine learning operations, such as pattern matching operations, may be performed within a memory device.

20 Claims, 7 Drawing Sheets

(56) References Cited

U.S. PATENT DOCUMENTS

| | | |
|---|---|---|
| 2018/0075339 A1 | 3/2018 | Ma et al. |
| 2019/0087119 A1 | 3/2019 | Oh et al. |
| 2020/0075099 A1 | 3/2020 | Choi et al. |
| 2020/0272899 A1* | 8/2020 | Dunne ...................... G06F 8/61 |
| 2021/0263847 A1* | 8/2021 | Rehmeyer ........... G11C 11/4093 |

* cited by examiner

APPARATUSES, SYSTEMS, AND METHODS FOR MACHINE LEARNING USING ON-MEMORY PATTERN MATCHING

BACKGROUND

This disclosure relates generally to memory devices, including volatile memory, such as dynamic random access memory (DRAM). Data may be stored in individual memory cells of the DRAM. The memory cells may be organized in an array of rows and columns. Each memory cell in a row may be coupled to a word line and each memory cell in a column may be coupled to a bit line. Thus, every memory cell is coupled to a word line and a bit line. Data may be provided to and retrieved from the DRAM for performing various computations by a microprocessor, graphical processing unit, or other circuitry.

Machine learning generally encompasses a variety of methods for utilizing one or more computational models to classify or otherwise infer meaning from data. One or more models may be trained for use by machine learning algorithms (e.g., a neural network). Examples of models include, but are not limited to, an artificial neural network, a decision tree, and a support vector machine. In some cases, a model may include one or more algorithms. Typically, training the computing device includes providing a training data set. The computing device analyzes the training data set to develop the model. The trained model may then be used (by the same computing device or another computing device) to analyze new data sets to complete the one or more tasks. The training may be supervised or unsupervised.

In examples of supervised training, each piece of data in the training data set includes an input and a desired output. The training data set is analyzed by a computing device to develop a model that generates the desired outputs from the inputs. For example, a computing device may be trained to diagnose lesions in magnetic resonance (MR) images of livers. A training data set may include a variety of images of livers where some of the images are livers having lesions and other images are of healthy livers with no lesions. Each of the images may be labeled as to whether the image includes or does not include a lesion. The computing device analyzes the images and generates one or more models that can properly classify the images as either including or not including a lesion, based in part, on the labels. The trained model may then be used to diagnose liver lesions in patients based on new MR liver images.

In examples of unsupervised training, each piece of data in the training data set includes only an input and no desired output. The computing device then analyzes the training data set to determine if there are common patterns in the pieces of data or at least some of the pieces of the data. For example, sets of electroencephalogram (EEG) readings from epilepsy patients may be provided to the computing device. The computing device may analyze the EEG readings to determine if there are patterns or similarities in some or all of the EEG readings. The computing device may generate one or more models that sorts the EEG readings into different groups based on the patterns or similarities of the EEG readings in those groups. The grouping of the EEG readings by the computing device may reveal certain patterns are associated with different epilepsy types and the trained models may be deployed to determine an epilepsy type based on new EEG readings.

Many machine learning methods, including supervised and unsupervised learning, utilize pattern matching in data (e.g., learning patterns in images associated with lesions, discovering patterns that reoccur in multiple EEG readings). Currently, data to be searched for patterns by the computing device is provided from a long term data storage device to the DRAM to processing circuitry where pattern matching operations are performed.

DETAILED DESCRIPTION

Figure 1:
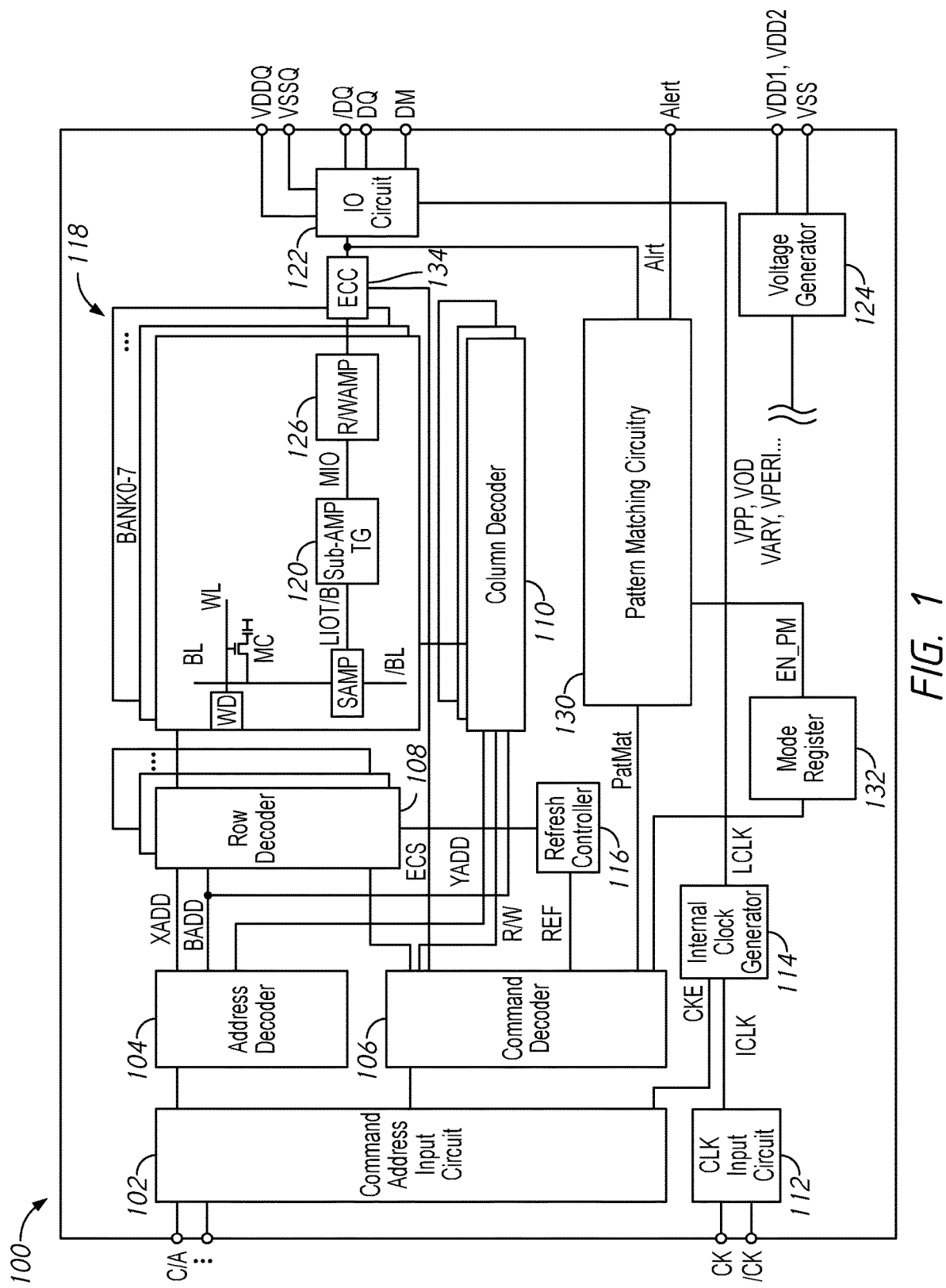
FIG. 1 is a block diagram of a semiconductor device according to embodiments of the present disclosure.

The following description of certain embodiments is merely exemplary in nature and is in no way intended to limit the scope of the disclosure or its applications or uses. In the following detailed description of embodiments of the present systems and methods, reference is made to the accompanying drawings which form a part hereof, and which are shown by way of illustration specific embodiments in which the described systems and methods may be practiced. These embodiments are described in sufficient detail to enable those skilled in the art to practice presently disclosed systems and methods, and it is to be understood that other embodiments may be utilized and that structural and logical changes may be made without departing from the spirit and scope of the disclosure. Moreover, for the purpose of clarity, detailed descriptions of certain features will not be discussed when they would be apparent to those with skill in the art so as not to obscure the description of embodiments of the disclosure. The following detailed description is therefore not to be taken in a limiting sense, and the scope of the disclosure is defined only by the appended claims.

Dynamic random access memory (DRAM) is often used to store data for performing or generated from computations performed by a microprocessor, graphical processing unit, application specific integrated circuit, and/or other circuitry (collectively referred to herein as processing circuitry). Data may be transferred to and from the DRAM from the processing circuitry and/or a long term data storage device (e.g., non-volatile memory). For example, data may be retrieved from a hard drive and provided to the DRAM. The data may then be provided to the processing circuitry from the DRAM as needed for computations performed by the processing circuitry. In some devices, providing data to and from the DRAM may be controlled by a memory controller. The memory controller may be integrated into the processing circuitry and/or a separate component in communication with the DRAM and the processing circuitry. The processing circuitry may perform computations according to executable instructions. The executable instructions may be included in a machine learning application, which may be stored on a computer readable medium accessible to the processing circuitry. The executable instructions may implement a training method, a trained model, and/or other machine learning operations.

Many machine learning methods, including supervised and unsupervised learning, utilize pattern matching in data. For example, data sets may be pre-processed prior to training and/or inference to remove features with no variation or remove data sets with missing information. In another example, patterns may be identified in a data set in order to identify a feature or other relevant portion of the dataset for use by a model to classify the data set and/or further train the model. Of course, pattern matching may be performed in other machine learning methods or at other points in the machine learning operations. Currently, data to be searched for patterns indicated by the machine learning application are provided from the long term data storage device to the DRAM to the processing circuitry where pattern matching operations are performed. However, machine learning applications often require significant amounts of data. For example, a single MR image may have several megabytes of data and a training data set may include hundreds or thousands of MR images. Transferring the data between components may slow down the pattern matching computations and in turn slow down and/or delay other machine learning operations. Accordingly, it would be desirable to reduce the data transferred between the components. In some applications, this may reduce the time utilized by machine learning applications and/or portions of machine learning applications (e.g., pre-processing tasks).

According to embodiments of the present disclosure, a memory, such as DRAM, may include circuitry for performing pattern matching computations (e.g., operations), referred to herein as pattern matching circuitry. In some embodiments, the pattern matching circuitry may include a comparator circuit and one or more registers in communication with the comparator circuit. The memory may receive a pattern from a machine learning application and data to be analyzed to determine whether or not the pattern is present in the data (e.g., the data includes one or more pattern matches). The machine learning application may include instructions encoded on computer readable media that are executed by processing circuitry and/or a memory controller. The pattern matching may be performed by (e.g., on or on board) the memory and the data to be analyzed need not be provided outside the memory to other processing circuitry for pattern matching operations. Rather, in some embodiments, only the results of the pattern matching operations may be provided by the memory to the machine learning application. The machine learning application may then use the result to perform additional machine learning operations (e.g., adjust weights in a layer of a neural network, remove features). In some applications, performing the pattern matching operations by memory and only providing the results may reduce the time required for pattern matching operations and/or machine learning applications at least because less data is transferred between the memory and the processing circuitry.

FIG. 1 is a block diagram showing an overall configuration of a semiconductor device 100 according to at least one embodiment of the disclosure. The semiconductor device 100 may be a semiconductor memory device, such as a DRAM device integrated on a single semiconductor chip.

The semiconductor device 100 includes a memory array 118. The memory array 118 is shown as including a plurality of memory banks. In the embodiment of FIG. 1, the memory array 118 is shown as including eight memory banks BANK0-BANK7. More or fewer banks may be included in the memory array 118 in other embodiments. Although FIG. 1 illustrates only one memory array 118, it is understood that the device 100 may include multiple memory arrays 118 in other embodiments. Each memory bank includes a plurality of word lines WL, a plurality of bit lines BL and /BL, and a plurality of memory cells MC arranged at intersections of the plurality of word lines WL and the plurality of bit lines BL and /BL, The selection of the word line WL is performed by a row decoder 108 and the selection of the bit lines BL and /BL is performed by a column decoder 110. A selected word line WL may be driven to a desired charge by word line driver WD. In the embodiment of FIG. 1, the row decoder 108 includes a respective row decoder for each memory bank and the column decoder 110 includes a respective column decoder for each memory bank. The bit lines BL and /BL are coupled to a respective sense amplifier (SAMP).

Read data from the bit line BL or /BL, is amplified by the sense amplifier SAMP, and provided to sub-amplifier transfer gate 120 over complementary local data lines (LIOT/B). The sub-amplifier transfer gate 120 may act as a switch to form a conductive path between the appropriate LIOT/B and appropriate shared main data lines (MIO). Read data may pass from the local data lines LIOT/B to the main data lines MIO via a conductive path provided by the sub-amplifier transfer gate 120 to a read amplifier 126, which provides the data to an IO circuit 122. Write data received from IQ circuit 122 is output from a write amplifier 126 and provided to the sense amplifier SAMP over the complementary main data lines MIO, the sub-amp transfer gate 120, and the complementary local data lines LIOT/B, and written in the memory cell MC coupled to the bit line BL or /BL.

The semiconductor device 100 may employ a plurality of external terminals for transmitting and receiving information from devices external to semiconductor device 100 (e.g., outside or off the memory), such as a memory controller (not shown in FIG. 1). The external terminals may include command and address (C/A) terminals coupled to a command and address bus to receive commands and addresses, and a CS signal, clock terminals to receive clocks CK and/CK, data terminals DQ to provide data, an alert pin ALERT for providing an Alrt signal, and power supply terminals to receive power supply potentials VDD1, VDD2, VSS, VDDQ, and VSSQ.

The clock terminals are supplied with external clocks CK and /CK that are provided to an input circuit 112. The external clocks may be complementary. The input circuit 112 generates an internal clock ICLK based on the CK and /CK clocks. The ICLK clock is provided to the command decoder 110 and to an internal clock generator 114. The internal clock generator 114 provides various internal clocks LCLK, based on the ICLK clock. The LCLK clocks may be used for timing operation of various internal circuits. The internal data clocks LCLK are provided to the input/output circuit 122 to time operation of circuits included in the input/output circuit 122, for example, to data receivers to time the receipt of write data.

The C/A terminals may be supplied with memory addresses. The memory addresses supplied to the C/A terminals are provided, via a command/address input circuit 102, to an address decoder 104. The address decoder 104 receives the address and supplies a decoded row address XADD to the row decoder 108 and supplies a decoded column address YADD to the column decoder 110. The address decoder 104 may also supply a decoded bank address BADD, which may indicate the bank of the memory array 118 containing the decoded row address XADD and column address YADD. The C/A terminals may be supplied with commands. Examples of commands include access commands for accessing the memory, such as read commands for performing read operations and write commands for performing write operations, as well as other commands and operations. The access commands may be associated with one or more row address XADD, column address YADD, and bank address BADD to indicate the memory cell(s) to be accessed.

The commands may be provided as internal command signals to a command decoder 106 via the command/address input circuit 102. The command decoder 106 includes circuits to decode the internal command signals to generate various internal signals and commands for performing operations. For example, the command decoder 106 may provide a row command signal to select a word line WL and a column command signal to select a bit line BL. In another example, the command decoder 106 may provide a mode register command provided to a mode register 132 to select a memory operating condition, such as a memory condition that enables pattern matching operations according to embodiments of the present disclosure.

The device 100 may receive an access command which is a read command. When an activation command is received, and row and bank addresses are timely suppled with the activation command, followed by a read command and a column address is timely supplied with the read command, read data is read from memory cells MC in the memory array 118 corresponding to the row address and column address. The read command is received by the command decoder 106 (e.g., command controller), which provides internal commands so that read data from the memory array 118 is provided to the read amplifier 128. The read data is output to outside from the data terminals DQ via the input/output circuit 122.

The device 100 may receive an access command which is a write command. When an activation command is received, and row and bank addresses are timely suppled with the activation command, followed by a write command and a column address is timely supplied with the write command, write data supplied to the data terminals DQ is written to a memory cells in the memory array 118 corresponding to the row address and column address. The write command is received by the command decoder 106, which provides internal commands so that the write data is received by data receivers in the input/output circuit 122. Write clocks may also be provided to the external clock terminals for timing the receipt of the write data by the data receivers of the input/output circuit 122. The write data is supplied via the input/output circuit 122 to the write amplifier 126, and by the write amplifier 126 to the memory array 118 to be written into the memory cell MC.

The device 100 may also receive commands causing it to carry out a refresh operation. The refresh signal REF may be a pulse signal which is activated when the command decoder 106 receives a signal which indicates an auto-refresh and/or other refresh command. In some embodiments, the refresh command may be externally issued to the memory device 100. In some embodiments, the refresh command may be periodically generated by a component of the device 100. The refresh signal REF is provided to the refresh controller circuit 116. A refresh command provided to the refresh controller circuit 116 may cause the device 100 to carry out refresh operations for one or more of the memory banks.

The refresh control circuit 116 supplies a refresh row address RXADD to the row decoder circuit 108, which may refresh one or more word lines WL, indicated by the refresh row address. The refresh control circuit 116 may control a timing of the refresh operation based on the refresh signal. Responsive to an activation of the refresh signal, the refresh control circuit 116 may generate and provide one or more refresh addresses.

One type of refresh operation may be an auto-refresh operation. Responsive to an auto-refresh operation the device 100 may refresh a word line or a group of word lines of the memory array 118, and then may refresh a next word line or group of word lines of the memory responsive to a next auto-refresh operation. The refresh control circuit 116 may provide an auto-refresh address as the refresh address which indicates a word line or a group of word lines in the memory array 118. The refresh control circuit 116 may generate a sequence of refresh addresses such that over time the auto-refresh operation may cycle through all the word lines of the memory array 118.

The device 100 may include error correction circuitry (ECC) 134 for detection and correction of errors in data written to and read from the memory array 118. The memory array 118 may include regions dedicated to storing parity information or device 100 may include an additional array for storing parity information (not shown). The ECC 134 may, receive data from the memory array 118 and the parity information. When the ECC 134 detects an error in the data, the ECC 134 may correct the error and rewrite the corrected data back to the memory array 118. The ECC 134 may detect and correct errors responsive to read and/or write commands provided by the command decoder 106. The ECC 134 may periodically retrieve data from the memory array 118 to detect and correct errors in the memory array independent of read and/or write commands. For example, the command decoder 106 may periodically issue an error correction signal ECS to the ECC 134, Similar to the auto-refresh operation described above, the ECC 134 may cycle through all of the word lines of the memory array 118 over a series of error correction signals.

A mode register 132 may be used to define various modes of for the device 100. The mode register 132 may retain the stored information until it is reprogrammed, reset, or the device 100 loses power. The mode register 132 may be written via a mode register write command. The mode register 132 may include one or more registers for storing information related to the different memory operations or configurations. For example, the mode register 132 may be used to set burst length, burst type, latency, frequency set point, enable programmable termination components, enable certain memory operations, as well as others. The mode register 132 may also be programmed with information that can be read to provide status information about the device 100. For example, the mode register 132 may be used, to provide a ready status, calibration status, as well as other status information. The information that is read may be programmed by circuits of the device 100. The mode register 132 may be read via a mode register read command. Reading the mode register 132 allows information about the status of operations and configurations to be provided by the device 100.

The mode register 132 may be used to specify a mode of operation in which pattern matching operations are performed by pattern matching circuitry 130. For example, when a particular value is written to the mode register 132, pattern matching operations may be implemented by the pattern matching circuitry 130 using signals provided to the memory, and when a different particular value is written to the mode register 132, the pattern matching operations may not occur (e.g., the pattern matching circuitry 130 may be disabled). A pattern matching operation may be performed by the pattern matching circuitry 130 in response to a one or more pattern matching commands in some embodiments. When the mode register 132 is programmed to enable pattern matching operations, the mode register 132 may provide a control signal EN_PM that enables pattern matching circuitry 130, which may include one or more registers and one or more comparator circuits (not shown in FIG. 1). When the pattern matching circuitry 130 is enabled by the control signal EN_PM from the mode register 132, the pattern matching circuitry 130 may respond to one or more pattern matching commands PatMat provided by the command decoder 106. Responsive to the one or more pattern matching commands, the pattern matching circuitry 130 may store a pattern in a register, perform a pattern matching operation on data stored in the memory array 118 to determine if the pattern is present in the data stored in the memory array 118, write a result of the pattern matching operation to a register, alter data in the array 118 based on the result of the pattern matching operation, provide the result from the register to the IO circuit 122, and/or provide an alert signal Alrt to an alert pin.

The pattern matching circuitry 130 may form an integral part of the device 100. For example, the pattern matching circuitry 130 may be formed in a same semiconductor die as the memory array 118, In some examples, the pattern matching circuitry 130 may be on a same printed circuit board as the memory array 118. In this manner, the pattern matching circuitry may be closer to a memory array than a processor or host device may be. For example, a latency or access time between the pattern matching circuitry 130 and the memory array 118 may be expected to be less than a latency or access time for passing data from the memory array 118 to output pins or external terminals of the device 100, such as when the data is provided to a processor or host external to the memory.

In some examples, data from the memory array 118 may be provided to the pattern matching circuitry 130 responsive to a read command and/or an internal read command. By "internal read" it is meant that data is retrieved from the memory array 118, but the data remains on device 100. That is, the data is not transmitted external to the memory, for example, via data terminals 24. For example, responsive to a read compare command, data may be provided from the memory array 118 to pattern matching circuitry 130. In some examples, a refresh operation, in addition to activating the word lines to refresh the data stored therein, the data may be provided to the pattern matching circuitry 130 for pattern matching operations. That is, during the refresh operation, the data may be "internally read" by the device 100 when the word lines are activated for refreshing. In some examples, during error correction operations, in addition to being provided to the ECC 134, the data may be provided to the pattern matching circuitry 130 for pattern matching operations. In some examples, data for pattern matching operations may be provided to the pattern matching circuitry 130 responsive to both refresh operation and error correction operations. The manner of providing data for pattern matching operations may be defined by one or more pattern matching commands provided by the command decoder 106.

The source of data or patterns for pattern matching operations may be defined by one or more pattern matching commands provided by the command decoder 106. For example, the source of the pattern may be from the data terminals 24 via IO circuit 122, the memory array 118, and/or a second memory array (not shown). In some examples the data for the pattern matching operations may be received via the data terminals 24 via IO circuit 122 responsive to a write compare command. During a write compare operation, data is received from the data terminals 24 and provided to the pattern matching circuitry 130 for performing the pattern matching operation however, the data is not written to the memory array 118.

In some examples, mode register commands, pattern matching commands, and/or other commands provided by the command decoder 106 may be responsive to commands (e.g., control signals) received from a memory controller (not shown in FIG. 1, see FIG. 3) external to the device 100. Data may be received from and provided to the memory, controller. According to embodiments of the present disclosure, the data and commands provided by the memory controller may be based, at least in part, on executable instructions of a machine learning application executed by processing circuitry in communication with the memory controller.

Power supply terminals of device 100 are supplied with power supply potentials VDD1, VDD2, and VSS. The power supply potentials VDD1, VDD2, and VSS are supplied to an internal voltage generator circuit 124. The internal voltage generator circuit 124 generates various internal potentials VPP, VOD, VARY, VPERI, and the like based on the power supply potentials VDD1, VDD2, and VSS supplied to the power supply terminals. While the various internal potentials and power supply potentials may be used for any of the different circuits of the device 100, the internal potential VPP is mainly used in the row decoder 108, the internal potentials VOD and VARY are mainly used in the sense amplifiers SAMP included in the memory array 118, and the internal potential VPERI is used in many peripheral circuit blocks.

The power supply terminals are also supplied with power supply potentials VDDQ and VSSQ. The power supply potentials VDDQ and VSSQ are supplied to the input/output circuit 122. The power supply potentials VDDQ and VSSQ supplied to the power supply terminals may be the same potentials as the power supply potentials VDD and VSS supplied to the power supply terminals in an embodiment of the disclosure. The power supply potentials VDDQ and VSSQ supplied to the power supply terminals may be different potentials from the power supply potentials VDD and VSS supplied to the power supply terminals in another embodiment of the disclosure. The power supply potentials VDDQ and VSSQ supplied to the power supply terminals are used for the input/output circuit 122 so that power supply noise generated by the input/output circuit 122 does not propagate to the other circuit blocks.

The components of semiconductor device 100 (e.g., command decoder 106, mode register 132, pattern matching circuitry 130) may transmit and/or receive information with other components of semiconductor device 100 without accessing the external terminals (e.g., C/A, DQ). In some embodiments, the components may be coupled to one another by conductive traces for transmitting and/or receiving information (e.g., the PatMat line, IN PM line, XADD line). Components that can communicate with other components of semiconductor device 100 without accessing the external terminals may be considered on semiconductor device 100 (e.g., "on memory" or "of the memory" when semiconductor device 100 is a memory device) and other components or devices that must access the external terminals of semiconductor device 100 to communicate with components of semiconductor device 100 may be considered off and/or outside semiconductor device 100 (e.g., "off memory" when semiconductor device 100 is a memory device).

Figure 2:
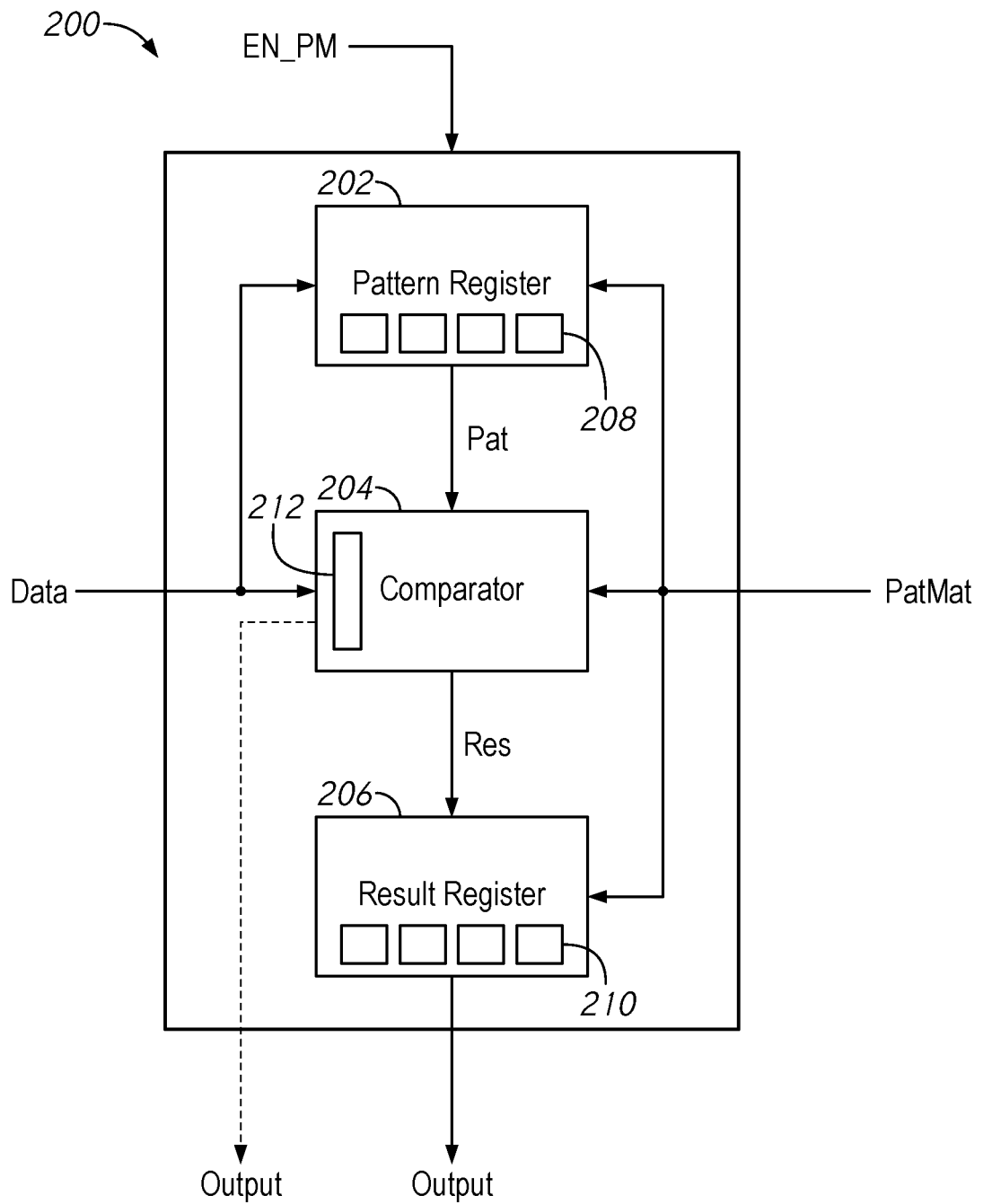
FIG. 2 is a block diagram of pattern matching circuitry according to embodiments of the present disclosure.

FIG. 2 is a block diagram of pattern matching circuitry 200 according to embodiments of the present disclosure. In some embodiments, pattern matching circuitry 200 may be included in pattern matching circuitry 130 shown in FIG. 1. The pattern matching circuitry 200 may include a pattern register 202, a comparator 204, and a result register 206.

The pattern matching circuitry 200 may be enabled by a control signal EN_PM, In some embodiments, the control signal may be provided by a mode register, such as mode register 132. The pattern matching circuitry 200 may ignore pattern matching commands when the control signal EN_PM is inactive (e.g., pattern matching circuitry 200 may be disabled). The pattern matching circuitry 200 may receive one or more pattern matching commands PatMat. In some embodiments, the pattern matching commands PatMat may be provided by a command decoder, such as command decoder 106. The pattern matching circuitry 200 may receive data, which may be provided to the pattern register 202 and/or comparator 204. The data may be provided from a memory array, such as memory array 118 and/or an IO circuit such as IO circuit 122.

The pattern register 202 may store one or more patterns to be used in a pattern matching operation. In some embodiments, the pattern register 202 may include multiple registers 208. Each register 208 may store one or more patterns. In some embodiments, the pattern register 202 may include a multipurpose register (MPR). In these embodiments, a pattern may be written to the pattern register 202 using an MPR write command. In other embodiments, a pattern may be written to the pattern register 202 responsive to a pattern register write command.

The comparator 204 may receive the pattern Pat from the pattern register 202 and data. The comparator 204 may perform a pattern matching operation to determine if the data includes Pat. In some embodiments, the comparator 204 may perform pattern matching operations for multiple patterns Pat, for example, when pattern register 202 includes more than one pattern. The pattern matching operations on multiple patterns may be performed sequentially or in parallel. In some embodiments, the comparator 204 may be hard coded to perform a single type of pattern matching operation. In other embodiments, the comparator 204 may be programmed (e.g., via a pattern matching command PatMat) to perform a particular type of pattern matching operation. The type of pattern matching operation may determine a type of comparison performed (e.g., find exact matches of Pat, find matches within a certain percentage of Pat, if Pat is a vector, find vectors in the data within a certain distance of the vector). Based on the determination of the pattern matching operation, the comparator may generate a result Res. In some embodiments, Res may include a count value of a number of times Pat is present in the data, a memory address of a location of a match of Pat in the data, a flag, and/or a combination thereof.

In some embodiments, the type of pattern matching operation may define the type of result generated as Res and/or other actions to be taken by the pattern matching circuitry 200 based on the result of the pattern matching operation. For example, in some embodiments, the pattern matching circuitry 200 may delete contents of the memory array where the data matches Pat or writing a pre-determined value to the memory array where the data matches Pat.

In some embodiments, the pattern matching command PatMat may define a source from which data is retrieved from for the pattern matching operation (e.g., the memory array and/or IO lines). In some embodiments, the pattern matching command PatMat may define a manner in which the data is retrieved such as via read operations, read compare operations, error correction operations, refresh operations. In some embodiments, the pattern matching command PatMat may define a number of operations performed to retrieve the data prior to performance of the pattern matching operation. For example, PatMat may indicate that data is to be received from the memory array responsive to a refresh operation. However, the refresh operation may only refresh one word line at a time, but a pattern to be matched may include data equivalent to four word lines. Thus, PatMat may further indicate that the pattern matching circuitry 200 may wait for four refresh operations prior to performing the pattern matching operation. In some embodiments, the pattern matching circuitry 200, and/or the comparator 204 of the pattern matching circuitry 200, may include a buffer 212 for storing the data received by the prior operations.

In some embodiments, the comparator 204 may include comparator logic such as a plurality of XOR logic circuits. The number of logic circuits may be based, at least in part, on a length (e.g., number of bits) in the pattern to be matched. In some embodiments, the comparator 204 may include one or more content addressable memory (CAM) cells. Other logic circuits or other circuit components (e.g., operational amplifiers) may be included in the comparator 204 in some embodiments.

The result register 206 may store one or more results Res output by the comparator 204 responsive to the pattern matching operation. In some embodiments, the result register 206 may include multiple registers 210. Each register 210 may store one or more results. In some embodiments, the result register 206 may include a multipurpose register (MPR). In these embodiments, a result register 206 may be read using an MPR read command. In other embodiments, a result may be read from the result register 206 responsive to a result register read command. In some embodiments, the result may be provided as Output. In some embodiments, the result register 206 may provide the Output to an IO circuit, such as IO circuit 122. In some embodiments, the result register 206 may provide the Output to the memory array. In some embodiments, the result register 206 may generate a signal, such as an alert signal as the Output. The alert signal may be provided to an alert pin (see FIG. 1) in some embodiments.

Optionally, in some embodiments, the comparator 204 may provide the Output in addition to or instead of the result register 206. In these embodiments, the result register 206 may optionally be omitted.

Figure 3:
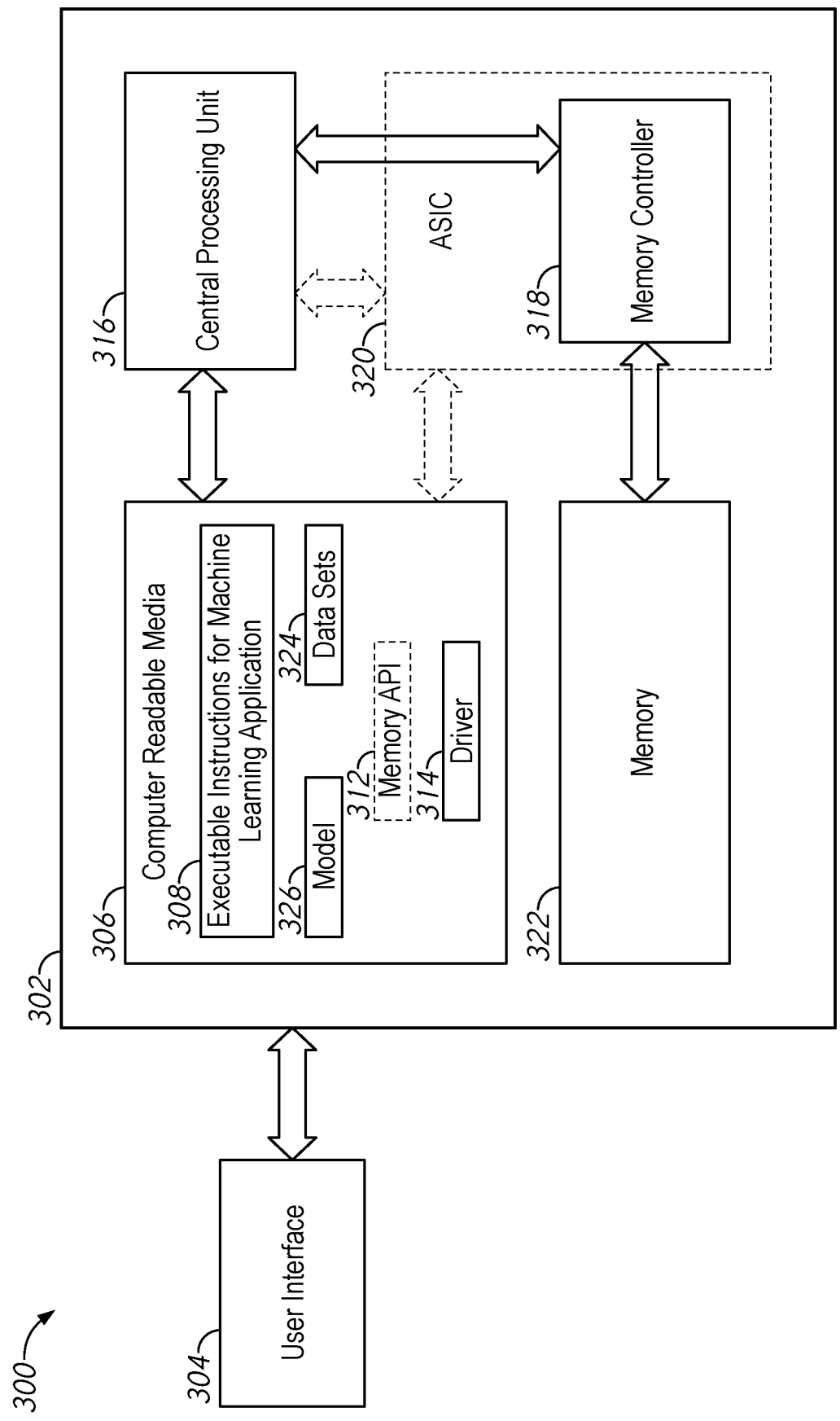
FIG. 3 is a block diagram of a system according to embodiments of the present disclosure.

FIG. 3 is a block diagram of a system 300 according to embodiments of the present disclosure. The system 300 may include a computing device 302 and a user interface 304. The computing device 302 may include computer readable media 306, a central processing unit (CPU) 316, a memory controller 318, and a memory 322. In some embodiments, the computing device 302 may further include an application specific integrated circuit (ASIC) 320. In some embodiments, the computing device 302 may include the ASIC 320 instead of the CPU 316. While a CPU is illustrated in FIG.

3, generally any number or kind of processor(s) may be used. In some embodiments, when the computing device 302 includes the ASIC 320, the memory controller 318 may be integrated with the ASIC 320. In other embodiments, the memory controller 318 may be separate from the ASIC 320. In some embodiments, the memory 322 may include at least a portion of device 100 and/or pattern matching circuitry 200.

The user interface 304 may provide outputs of the computing device 302 to a user and provide inputs from the user to the computing device 302. In some embodiments, the user interface 304 may include a display (e.g., LCD, CRT) and/or speakers for providing outputs. In some embodiments, the user interface 304 may include user controls for providing inputs such as a keyboard, touch screen, keyboard, mouse, and/or track pad.

The computer readable media 306 may be implemented using any media, including non-transitory computer readable media. Examples include memory, read only memory (RAM), read only memory (ROM), volatile or non-volatile memory, hard drive, solid state drives, or other storage. While a single computer readable media 306 is shown in FIG. 3, multiple media may be present and the executable instructions described herein may be provided on one or more computer readable media. The computer readable media may be used to implement software and/or firmware components. In some embodiments, the computer readable media 306 may be encoded with instructions for implementing a driver 314. The driver 314 may provide instructions for an operating system of the computing device 302 for interacting with one or more components of the computing device 302 (e.g., CPU 316, memory controller 318, ASIC 320, and/or memory 322).

The CPU 316 may execute instructions encoded on the computer readable media 306. For example, instructions used to implement the driver 314. In some embodiments, the CPU 316 may include or may be replaced by one or more graphical processing units. The CPU 316 may provide and receive data from the memory 322 via the memory controller 318. The memory controller 318 may control how data is input and output from the memory 322. The memory controller 318 may issue commands to the memory 322, such as mode register write commands, read commands, write commands, and/or pattern matching operation commands.

In some embodiments, computing device 302 may include an ASIC 320 in addition to or instead of CPU 316. When the computing device 302 includes both the ASIC 320 and the CPU 316, the ASIC 320 may receive and provide signals to the CPU 316 and/or computer readable media 306. When the computing device 302 does not include the CPU 316, the ASIC 320 may perform computations responsive to instructions provided by the computer readable media 306. While in some embodiments, the ASIC 320 may have fewer computing capabilities than the CPU 316, the ASIC 320 may be smaller and/or require less power than the CPU 316. In some applications, such as mobile devices, the size and power advantages of the ASIC 320 may outweigh the computing advantages of the CPU 316. While an ASIC 320 is shown in FIG. 3, other processing circuitry may be used in other examples (e.g., one or more controllers, microcontrollers, field programmable gate array (FPGA) circuits).

According to embodiments of the present disclosure, the computer readable media 306 may be encoded with executable instructions for a machine learning application 308. The executable instructions may be executed, for example by the CPU 316, The machine learning application 308 may include instructions for implementing a neural network, generating a model based on a training data set, pre-processing data for training or analysis by a trained model, inferring meaning from input data based on a trained model, classifying input data based on a trained model, and/or other machine learning operations. In some embodiments, the computer readable media 306 may store one or more data sets 324, The data sets 324 may include data sets used by the machine learning application 308. The data sets 324 may include one or more training data sets for generating a model with the machine learning application 308 and/or one or more data sets for analysis by a trained model of the machine learning application 308.

In some embodiments, the computer readable media may be encoded with one or more models 326. In some embodiments, the model 326 may be included with the machine learning application 308. In other embodiments, such as the one shown in FIG. 3, the model 326 may be separate from the machine learning application 308. However, when the model 326 is separate from the machine learning application 308, the model 326 may be accessed and/or used by the machine learning application 308, for example, the machine learning application 308 may use the model 326 to classify data from data sets 324. In some embodiments, the model 326 may be trained and/or generated by the machine learning application 308. In some embodiments, the model 326 may be pre-existing. In some embodiments, the model 326 may have been generated and/or trained by a computing device other than computing device 302 and loaded onto the computer readable media 306. Example models that may be included in model 326 include, but are not limited to, an artificial neural network, a decision tree, and/or a support vector machine. For example, for a neural network, the model 326 may specify a number of layers of the neural network, how one or more nodes of the neural network are connected, weights assigned to inputs of nodes, and/or how the inputs are combined (e.g., weighted average). In some examples, the model 326 may specify criteria used to classify and/or perform an inference on input data (e.g., data from data sets 324), for example, regression, least squares, and/or K-means clustering.

In some embodiments, the computer readable media 306 may be encoded with executable instructions for a memory application programming interface (API) 312. The memory API 312 may allow the machine learning application 308 access and control over on-board pattern matching capabilities of the memory 322. For example, the memory API 312 may allow the machine learning application 308 to decide whether or not to utilize the on-board pattern matching capabilities of the memory 322 or perform pattern matching operations on the CPU 316. In another example, the memory API 312 may allow the machine learning application 308 to determine a type of pattern matching operation to be performed by the memory 322. In some embodiments, the memory API 312 may translate executable instructions generated by human-readable programming languages (e.g., Python) into instructions that may allow the memory controller 318 to provide memory commands (e.g., mode register write commands, pattern register write commands, pattern matching commands) to the memory 322. In some embodiments, the memory API 312 may be included within the machine learning application 308. In some embodiments, the machine learning application 308 automatically determines whether and how to utilize the on-board pattern matching capabilities of the memory 322 and the memory API 312 may be omitted.

Figure 4:
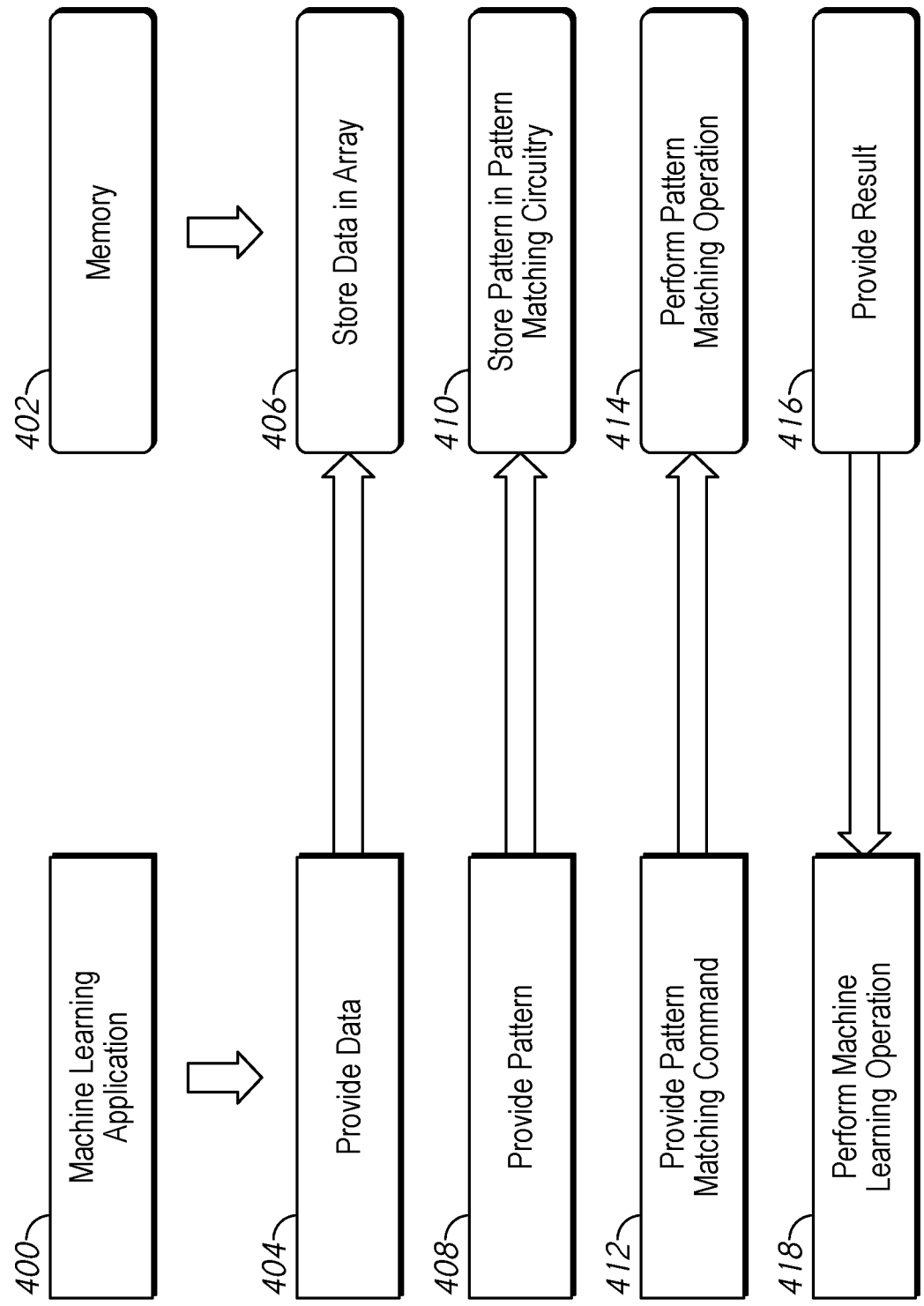
FIG. 4 is a diagram illustrating interactions between a machine learning application and a memory with on-board pattern matching capabilities according to embodiments of the present disclosure.

FIG. 4 is a diagram illustrating interactions between a machine learning application and a memory with on-board pattern matching capabilities according to embodiments of the present disclosure. The machine learning application 400 may be included in machine learning application 308 in some embodiments. The machine learning application 400 may be executable instructions encoded on a computer readable medium (e.g., computer readable media 306) and the instructions may be executed by processing circuitry (e.g., CPU 316, ASIC 320). The memory 402 may be included in device 100 and/or memory 322.

At block 404, the machine learning application 400 may provide data to the memory 402 (e.g., cause the memory controller to provide data to the memory 402). In some embodiments, the data may be one or more data sets or a portion of a data set (e.g., data sets 324) stored on computer readable media. The memory 402 may store the received data in a memory array (e.g., array 118) at block 406. At block 408, the machine learning application 400 may provide a pattern to the memory 402. In some embodiments, the pattern may be included in the data set, a separate data set, or may be data generated by previously, performed machine learning operations. At block 410, the memory 402 may store the pattern in pattern matching circuitry of the memory 402. In some embodiments, the pattern may be stored in a register of the pattern matching circuitry. The pattern and/or data may be provided to the memory 402 based on instructions of the machine learning application 400 executed by processing circuitry and/or memory controller. In some embodiments, the data and/or pattern may be provided to the memory 402 from a separate computer readable media, cache or other storage of the processing circuitry, and/or a combination thereof. In some embodiments, the data and/or pattern may be provided via a memory controller (e.g., memory controller 318). In some embodiments, the pattern may be provided before the data and/or the pattern and data may be provided simultaneously.

At block 412, the machine learning application 400 may provide a pattern matching command to the memory 402. In some embodiments, the pattern matching command may be issued to the memory 402 by the memory controller based, at least in part, on instructions included in the machine learning application 400. Responsive, at least in part, to receiving the pattern matching command, the memory 402 may perform a pattern matching operation according to principles of the present disclosure at block 414. Although block 414 is shown below blocks 404 and 408, in some embodiments, the machine learning application 400 may provide the pattern matching command before the data and/or pattern are provided, In these embodiments, the memory 402 may wait for receipt of the data and/or pattern prior to performing the pattern matching operation responsive to the pattern matching command. In some embodiments, the pattern matching command may be provided at the same time as the pattern and/or data.

At block 416, the memory 402 may provide a result of the pattern matching operation. In some embodiments, the result may be an indication that the pattern was or was not present in the data. In some embodiments, the result may be an indication of a number of times the pattern was present in the data. Other result types or combinations thereof may also be provided in other embodiments. In some embodiments, the memory 402 may provide the result to a memory controller, which may provide the result to processing circuitry. Responsive, at least in part, to the result, the machine learning application 400 may perform machine learning operation (e.g., cause the processing circuitry to perform a machine learning operation) at block 418. For example, based on the result, the machine learning application 400 may adjust a model (e.g., model 326) being trained on the data provided to memory 402, such as changing a weight in a convolutional layer in a convolutional neural network. In another example, the machine learning application 400 may provide a final result to a user interface user interface 304) based, at least in part, on the result provided by, the memory 402. In some examples, the final result may be a classification or an inference, such as an indication that an image of a liver includes a lesion or an EEG trace indicates a particular type of epilepsy. In some examples, the final result may be generated, at least in part, by a model (e.g., model 326) included and/or accessed by the machine learning application 400.

Figure 5:
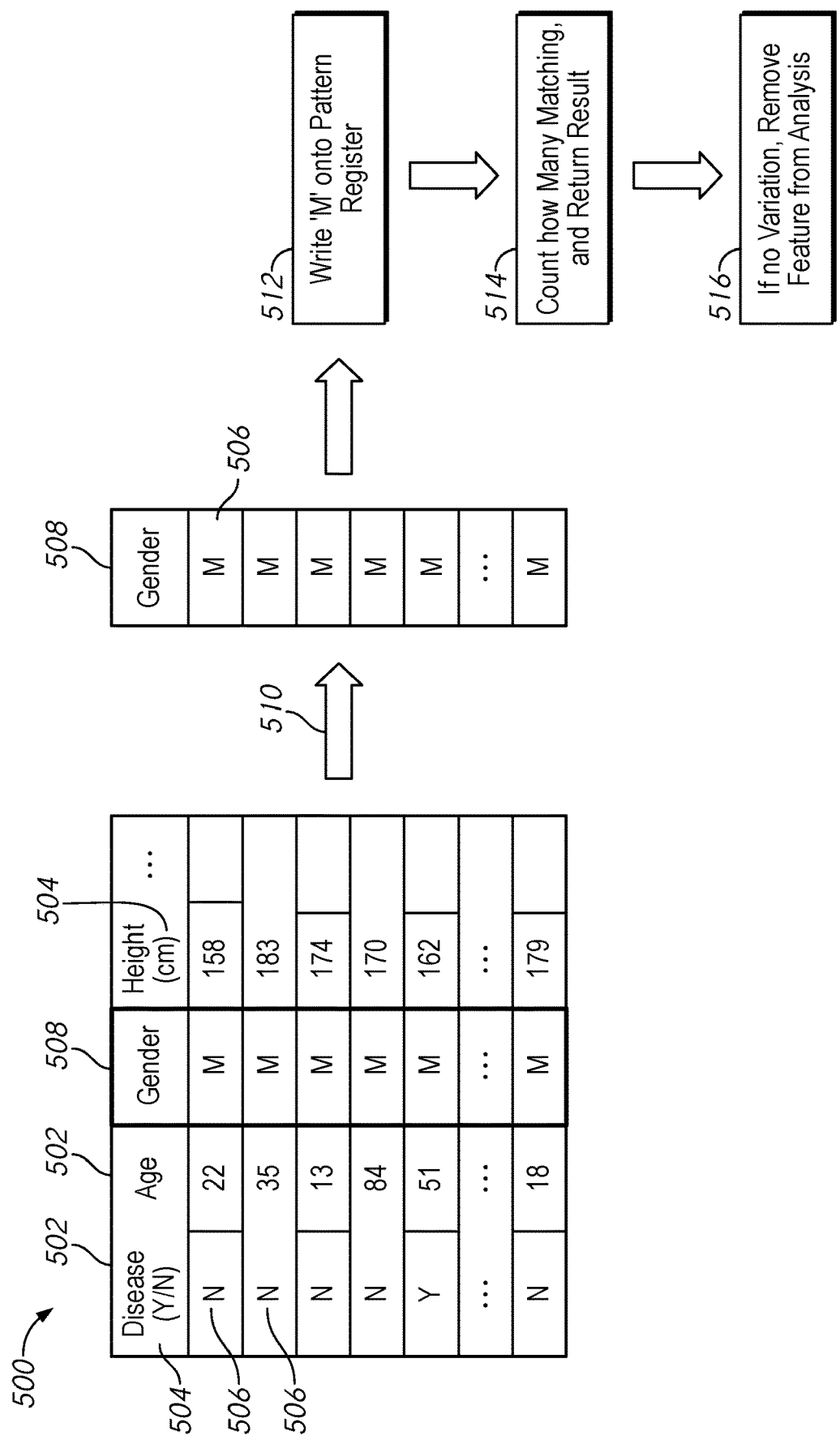
FIG. 5 is an example of a pre-processing machine learning operation that utilizes on-memory pattern matching according to embodiments of the present disclosure.
Figure 6:
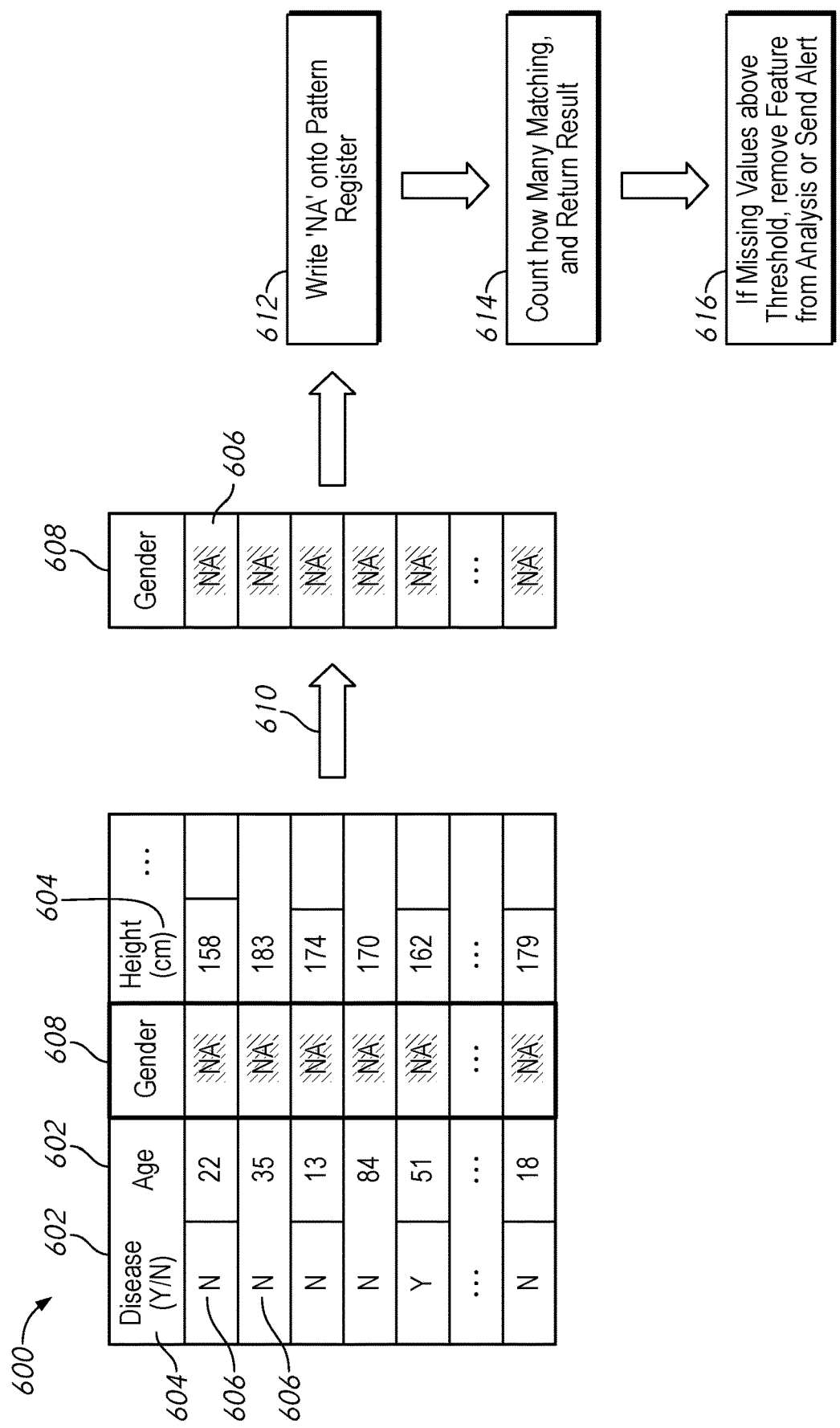
FIG. 6 is an example of a pre-processing machine learning operation that utilizes on-memory pattern matching according to embodiments of the present disclosure.
Figure 7:
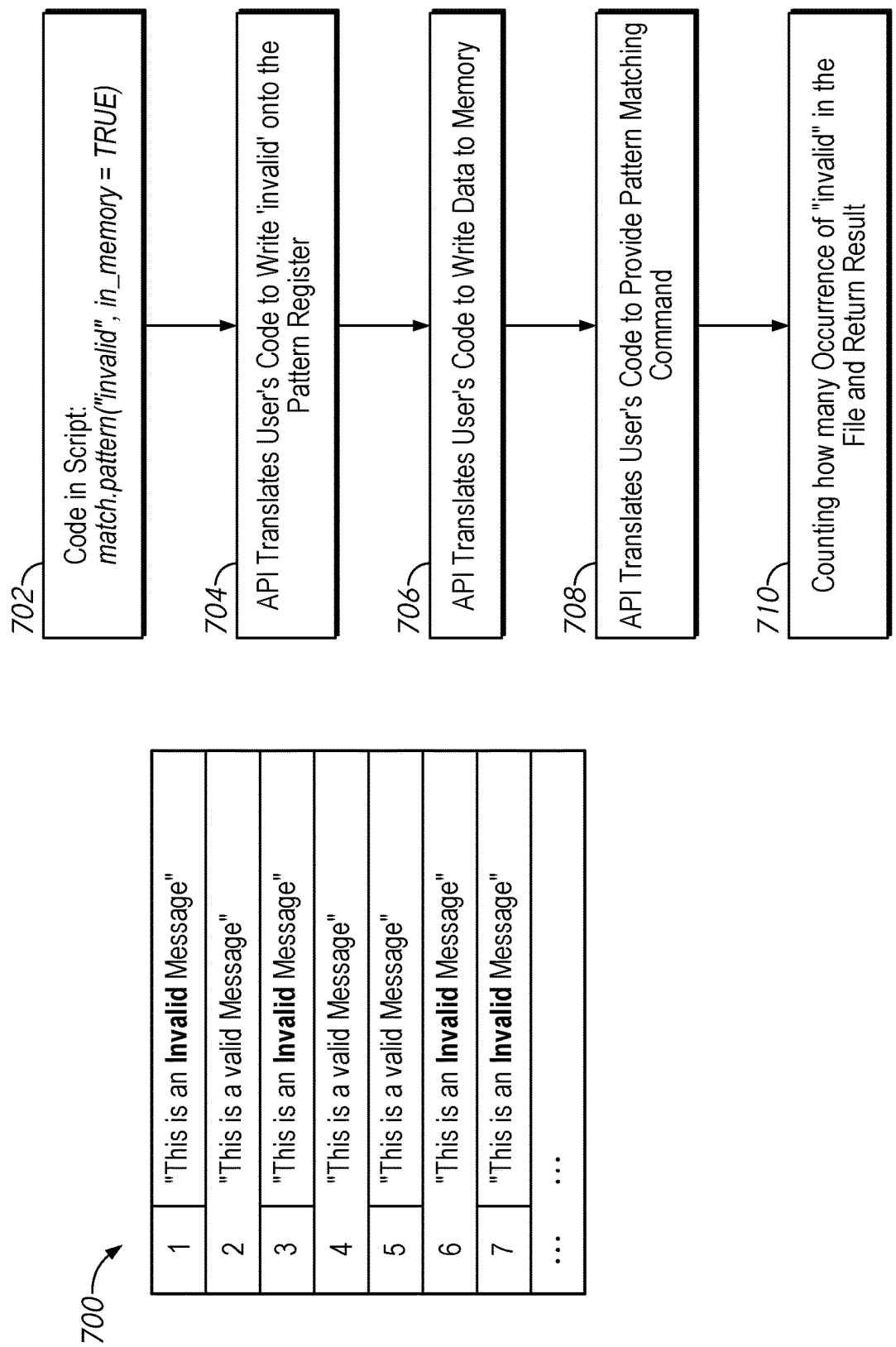
FIG. 7 is an example of a machine learning operation that utilizes on-memory, pattern matching according to embodiments of the present disclosure.

FIGS. 5-7 provide examples of machine learning applications utilizing on-memory pattern matching according to embodiments of the present disclosure. In some embodiments, the examples shown in FIGS. 5-7 may be performed at least in part by the components shown in FIGS. 1-4. The examples are provided for illustrative purposes only and the principles of the present disclosure are not limited to the examples provided.

Machine learning often involves significant pre-processing tasks. For example, data sets may be processed to remove data and/or change the formatting of the data prior to being used for training a machine learning model and/or being provided to a trained model for analysis. For example, a portion of the data set that does not contribute useful or significantly, useful information for training and/or inference to classify data may be removed and/or ignored.

FIG. 5 is an example of a pre-processing machine learning operation that utilizes on-memory pattern matching according to embodiments of the present disclosure. FIG. 5 illustrates an example of checking feature/column variations. A data set 500 may be organized in columns 502 where each column 502 corresponds to a different feature 504. In some embodiments, data set 500 may be included in data sets 324. In the example shown in FIG. 5, some of the features 504 include whether or not a disease is present, an age of a subject, a gender of the subject, and a height of the subject. Each row 506 may include entries for the features 504 for an individual subject.

In some embodiments, data set 500 may be a training data set. A machine learning application (e.g., machine learning application 400 and/or machine learning application 308) may be programmed to generate a model that provides an output that indicates whether or not the disease is present based on the other features 504 in data set 500. Prior to training and/or as a first step of the training process, the machine learning application may analyze the features 504 for variations through the corresponding columns 502. If a feature 504 does not show any variation across any of the subjects, then the feature 504 may not be providing any information relevant to generating the desired output (e.g., determining whether or not the disease is present). Thus, features 504 that have no variation may be removed from the data set and/or ignored when generating the model from the training data set. For example, the highlighted column 508 ("Gender") has no variation across the subjects.

To analyze the features 504 for variations, the data of each column 502 may be provided to a memory (e.g., device 100, memory 322, memory 402) for storing in an array (e.g., array 118). As indicated by arrow 510, a column, such as column 508, may be provided to the memory. The data in the first row 506 of column 508 may be provided as a pattern for a pattern register pattern register 202) included in pattern matching circuitry of the memory (e.g., pattern matching circuitry 130 and/or pattern matching circuitry 200). As indicated by block 512, 'M' from the first row 506 of column 508 may be written to the pattern register. The pattern matching circuitry of the memory may analyze (e.g., with comparator 204) the data of column 508 stored in the memory array and count how many rows 506 include data that matches the pattern 'M' and return a result which includes a number of matches found in column 508 as indicated by block 514. The result may be analyzed by the machine learning application, and if the number of matches to 'M' equals a number of rows 506 in column 508, the machine learning application may determine there is no variation in the feature 504 of column 508. The machine learning application may then remove the feature 504 from further analysis as indicated by block 516. For example, further analysis may include using the remaining data for generating a model (e.g., model 326) or analyzing the remaining data to classify data (e.g., make an inference) with a model (e.g., model 326).

The machine learning operations illustrated in FIG. 5 may be performed responsive to executable instructions encoded on a computer readable medium (e.g., computer readable media 306). The executable instructions may be based on code provided by a user. Example pseudo-code is provided below:

```
#For each column in the data table:
#Here X is the input data set
    current_column=get.each.column(X)
#Get the first element from the column
    first_element=get.first.word(current_column)
#Put the first element into pattern register and perform
    pattern matching in memory
    count=matchpattern(first_element,
        in_memory=TRUE)
    if count=number of rows, then delete this column
```

The machine learning application (e.g., machine learning application 308) and/or a memory API (e.g., memory API 312) may translate at least some of the code and/or executable instructions into commands that may be provided by the memory controller to the memory. For example, the API may understand the in_memory=TRUE flag and may cause the first element of the column to be written into the pattern register (which may be a multipurpose register in some embodiments) and cause the memory to perform the pattern matching operation. If a user did not wish to use the on-memory pattern matching, then in_memory=FALSE, and the user may include CPU/GPU=TRUE to indicate another component may perform the pattern matching operation.

FIG. 6 is an example of a pre-processing machine learning operation that utilizes on-memory pattern matching according to embodiments of the present disclosure. FIG. 6 illustrates an example of checking feature/column missing rates. A data set 600 may be organized in columns 602 where each column 602 corresponds to a different feature 604. In some embodiments, data set 600 may be included in data sets 324. In the example shown in FIG. 6, some of the features 604 include whether or not a disease is present, an age of a subject, a gender of the subject, and a height of the subject. Each row 606 may include entries for the features 604 for an individual subject. However, some entries for one or more features 604 may be missing, as indicated by the 'NA' label in the columns 602.

In some embodiments, data set 600 may be a training data set or a data set to be analyzed by a trained model to make one or more inferences. A machine learning application (e.g., machine learning application 308) may be programmed to generate a model that provides an output that indicates whether or not the disease is present based on the other features 604 in data set 600 or analyze the data set 600 and provide indications as to whether the individual subjects have the disease. Prior to generating a model or analyzing the data set 600 with an existing model (e.g., model 326), the machine learning application may analyze the columns 602 for missing entries. If a column 602 is missing too many entries, the corresponding feature 604 may not be used to generate the model or the existing model may not be able to accurately analyze the data. In some examples, the features 604 with missing rates above a threshold value (e.g., a percentage of the total number of entries) may be removed from the data set and/or ignored when generating a model from data set 600. In another example, if the feature 604 is used by the existing model for generating the desired output, then an error or warning indication may be provided to alert a user that the data set may not be analyzed and/or the results may be less accurate. For example, the highlighted column 608 ("Gender") has several missing entries across the subjects.

To analyze the features 604 for missing entries, the data of each column 602 may be provided to a memory (e.g., device 100, memory 322, memory 402) for storing in an array (e.g., array 118). As indicated by arrow 610, a column, such as column 608, may be provided to the memory. Data corresponding to an indication that an entry is missing may be provided as a pattern for a pattern register (e.g., pattern register 202) included in pattern matching circuitry of the memory (e.g., pattern matching circuitry 130 and/or pattern matching circuitry 200). As indicated by block 612 'NA' may be written to the pattern register as a pattern indicating that an entry from the column 608 is missing. The pattern matching circuitry of the memory may analyze the data of column 608 stored in the memory array and count how many rows 606 include data that matches the pattern 'NA' and return a result which includes a number of matches found in column 608 as indicated by block 614. The result may be analyzed by the machine learning application, and if the number of matches to 'NA' is equal to or greater than a threshold value, the machine learning application may determine there are too many missing entries in column 608 for the corresponding feature 604 of column 608 to be used to generate a model and/or for a model to analyze data set 600 (e.g., data set 600 may not be used for classifying data/making an inference). The machine learning application may then remove the feature 604 from further analysis (e.g., when generating the model) and/or send an alert to the user (e.g., error, warning) as indicated by block 616.

The machine learning operations illustrated in FIG. 6 may be performed responsive to executable instructions encoded on a computer readable medium (e.g., computer readable media 306). The executable instructions may be based on code provided by a user. Example pseudo-code is provided below:

```
#For each column in the data table:
#Here X is the input data set
    current_column=get.each.column(X)
#In memory 'NA' string matching,
    count=match.pattern('NA', in_memory=TRUE)
#Calculate percentage of missing
    miss_rate=count/total_number_sample
#Delete this column if miss_rate>some predefined threshold.
    If miss_rate>threshold
        delete this column;
```

As discussed in reference to FIG. 5, the machine learning application (e.g., machine learning application 308) and/or a memory API (e.g., memory API 312) may translate at least some of the code and/or executable instructions into commands that may be provided by the memory controller to the memory. For example, the API may understand the in_memory=TRUE flag and may cause the indication of missing data, 'NA', to be written to the pattern register and cause the memory to perform the pattern matching operation. However, other machine learning operations may be performed by the processing circuitry. For example, calculation of miss_rate, comparing the miss_rate to a threshold value, and/or deleting the column may be performed at least in part by the processing circuitry.

FIG. 7 is an example of a machine learning operation that utilizes on-memory pattern matching according to embodiments of the present disclosure. The data set 700 may, be a massive text file. In some embodiments, data set 700 may be included in data sets 324. In some embodiments, as part of a training process and/or as part of analyzing the data set 700 with a trained model, the data set may be searched for a particular string within the text (e.g., word or phrase).

An instruction in a machine learning application (e.g., machine learning application 308), may include instructions corresponding to a line of code written by a user, such as match.pattern("invalid", in_memory=TRUE) as indicated by block 702. Responsive to the code, the machine learning application and/or a memory API (e.g., memory API 312) may translate the code into commands that may be provided to a memory (e.g., device 100, memory 322, memory 402) by a memory controller (e.g., memory controller 318) The commands may cause a desired string to be written to a pattern register (e.g., pattern register 202) as indicated by block 704. In the example shown in FIG. 7, the desired string is 'invalid'. The API may translate the code to cause the data set 700 to be written to the memory (e.g., written to memory array 118). The API may translate the code to cause a pattern matching command to be provided to the memory as indicated by block 708. The pattern matching command may indicate a type of pattern matching operation and/or a type of result to be provided based on the pattern matching operation. Responsive, at least in part, to the pattern matching command, the pattern matching circuitry of the memory (e.g., pattern matching circuitry 130 and/or pattern matching circuitry 200) may analyze the data set 700 to determine if the desired string is present and return a result as indicated by block 710. In some embodiments, the result may be a number of times the string 'invalid' occurs in data set 700. In some embodiments, the result may be locations in the data set 700 where the string 'invalid' is present. In some embodiments, the result may include a combination thereof. The result provided by the memory may be returned to the machine learning application, and in some embodiments, a machine learning operation may be performed based on the result received.

In a conventional system, the machine learning operations described above in reference to FIGS. 5-7 would require loading data (e.g., data of column 508) to the memory, and then providing the data to processing circuitry (e.g., CPU 316) for pattern matching by the processing circuitry. This additional transfer of data between the memory and the processing circuitry may add a significant delay in completing the pattern matching operation, especially when the data set is large and/or the data for each element in a feature column (e.g., rows 506) is significant (e.g., image data). It may also require additional power consumption by the computing device. In some applications, after preprocessing data using on-memory pattern matching, transferring data off the memory may be required for further machine learning operations. However, the amount of data that needs to be transferred from the memory to the processor (e.g., via a memory controller) may be reduced, for example, as compared to when preprocessing is performed by the processor.

In a device and/or system using a machine learning application and on-memory pattern matching according to principles of the present disclosure, the use of on-memory pattern matching may allow the processing circuitry to perform other tasks while the pattern matching operation is occurring. That is, pattern matching may be performed by the memory in parallel with other machine learning operations performed by the processing circuitry. This may further decrease time utilized by machine learning applications.

Systems and/or devices described herein may be used to implement machine learning systems that could be put to any of a variety of applications. In some applications, data may be classified to identify medical conditions or states. For example, MRI or CT images may be analyzed by machine learning methods (e.g., trained neural network) to determine whether lesions (e.g., tumors, plaque) are present in anatomy present in the image. In another example, images of histology slides may be analyzed by machine learning methods to determine if cells in the slides exhibit dysplasia. In a further example, medical data, such as EEG or electrocardiogram (ECG) traces may be analyzed by machine learning methods to determine if a condition is present (e.g., seizure, arrhythmia).

In some applications, data may be classified to identify objects in one or more images. For example, autonomous vehicles may utilize systems described herein to identify people, buildings, cars, signs, obstacles, roads, sidewalks, and/or other objects in a driving environment. Images from one or more cameras of a vehicle may be provided to systems described herein. The systems described herein may include machine learning models trained to classify objects in a driving environment using on-memory pattern matching described herein to facilitate the classification.

In some applications, data may be classified to identify humans (e.g., faces) in one or more images. In some applications, faces or other features of the identified humans may be used to determine an identity of the human. For example, surveillance systems may utilize systems described herein to identify particular faces or individuals in a surveyed environment. Images from one or more surveillance cameras may be provided to systems described herein. The systems described herein may include machine learning models trained to classify faces or other human images to identify people. In some applications, the system may use the results provided by the machine learning models to approve or deny, access of an individual to a particular area (e.g., unlocking or refusing to unlock a door).

In some examples, data may be classified to identify one or more home automation states or actions to be taken. For example, home automation systems may utilize systems described herein to identify particular actions to take in a home environment. Data from one or more home sensors (e.g., temperature sensors, appliance usage data, image data) may be provided to systems described herein that may utilize models trained to classify particular states of the home environment. Systems described herein may accordingly control one or more home environment controls (e.g., security systems, HVAC systems, entry authorization systems) based on classification of the sensor data.

Of course, it is to be appreciated that any one of the examples, embodiments or processes described herein may be combined with one or more other examples, embodiments and/or processes or be separated and/or performed amongst separate devices or device portions in accordance with the present systems, devices and methods.

Finally, the above discussion is intended to be merely illustrative and should not be construed as limiting the appended claims to any particular embodiment or group of embodiments. Thus, while various embodiments of the disclosure have been described in particular detail, it should also be appreciated that numerous modifications and alternative embodiments may be devised by those having ordinary skill in the art without departing from the broader and intended spirit and scope of the present disclosure as set forth in the claims that follow. Accordingly, the specification and drawings are to be regarded in an illustrative manner and are not intended to limit the scope of the appended claims.

What is claimed is:

1. An apparatus comprising:
a memory including:
pattern matching circuitry configured to perform a pattern matching operation on data and a pattern provided to the memory and generate a result;
a mode register configured to provide a control signal to enable and disable the pattern matching circuitry;
at least one computer readable medium encoded with executable instructions for implementing a machine learning application; and
processing circuitry coupled to the computer readable medium and configured to execute a machine learning operation, in accordance with the machine learning application, using the result and the executable instructions.

2. The apparatus of claim 1, further comprising a memory controller configured to receive the result from the memory and provide the result to the processing circuitry.

3. The apparatus of claim 2, wherein the computer readable medium is further encoded with executable instructions for implementing a memory application programming interface (API), wherein the memory API is configured to translate executable instructions of the machine learning application into instructions that cause the memory controller to provide memory commands to the memory to perform the pattern matching operation.

4. The apparatus of claim 1, wherein the computer readable medium further encodes a data set, wherein the data provided to the memory for the pattern matching operation includes at least a portion of the data set.

5. The apparatus of claim 4, wherein the data set is a training data set and the result is used by the machine learning application to train a model.

6. The apparatus of claim 4, wherein the machine learning application uses a trained model and the result is used by the trained model to make an inference.

7. The apparatus of claim 1, wherein the computer readable medium further encodes a data set; wherein the pattern provided to the memory for the pattern matching operation includes at least a portion of the data set.

8. The apparatus of claim 7, wherein the machine learning application comprises a supervised learning application.

9. The apparatus of claim 7, wherein the machine learning application uses the result to classify the portion of the data set.

10. The apparatus of claim 1, wherein the memory includes a memory cell array configured to store the data and the pattern matching circuitry includes a register configured to store the pattern.

11. The apparatus of claim 1, wherein the machine learning operation comprises at least one of providing a final result, adjusting a model being trained by the machine learning operation, or removing a portion of the data from analysis.

12. The apparatus of claim 1, wherein the final result includes a classification of the data.

13. A system comprising:
at least one computer readable media encoded with instructions for a machine learning application and a data set;
processing circuitry configured to execute machine learning operations in accordance with the machine learning application;
a memory including a memory cell array and pattern matching circuitry configured to perform pattern matching operations, wherein the machine learning application includes a memory application programming interface configured to allow the machine learning application to utilize the pattern matching operations of the memory; and
a memory controller configured to:
provide commands to the memory to control the pattern matching operations;
provide data of the data set from computer readable media to the memory for storage in the memory cell array; and
provide a result of the pattern matching operations on the data from the memory to the processing circuitry, wherein the processing circuitry is configured to perform a machine learning operation based, at least in part, on the result.

14. The system of claim 13, further comprising a user interface, wherein a final result of the machine learning operation is provided to the user interface.

15. The system of claim 14, wherein the final result includes an inference or a warning that the data of the data set cannot be used to make the inference.

16. The system of claim 13, wherein the result includes a number of times a pattern occurs in the data and the machine learning operation includes removing the data if the number of times the pattern occurs equals a size of the data.

17. The system of claim 13, wherein the result includes a number of times entries are missing in the data and the machine learning operation includes removing the data if the number of times the entries are missing is equal to or greater than a threshold value.

18. The system of claim 13, wherein the data includes a text file and the result includes locations in the text file where a pattern is located.

19. The system of claim 13, wherein the processing circuitry includes an application specific integrated circuit (ASIC).

20. The system of claim 19, wherein the memory controller is integrated with the ASIC.

* * * * *